United States Patent
Thiel et al.

(10) Patent No.: US 6,644,517 B2
(45) Date of Patent: Nov. 11, 2003

(54) STEM CONFIGURATION TO REDUCE SEAL ABRASION IN METERED DOSE AEROSOL VALVES

(75) Inventors: Charles G. Thiel, Maplewood, MN (US); Peter D. Hodson, Trowell (GB); Andrew M. Bryant, Quorn (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/978,816

(22) Filed: Oct. 15, 2001

(65) Prior Publication Data

US 2002/0088828 A1 Jul. 11, 2002

Related U.S. Application Data

(60) Provisional application No. 60/240,737, filed on Oct. 16, 2000.

(51) Int. Cl.$^7$ ................................................. B65D 83/14
(52) U.S. Cl. .............................. 222/402.24; 222/402.2; 251/325
(58) Field of Search ..................... 222/402.2, 402.24; 251/325

(56) References Cited

U.S. PATENT DOCUMENTS

| | | | |
|---|---|---|---|
| 3,169,525 A | 2/1965 | Bowen | |
| 3,351,247 A | 11/1967 | Frangos | |
| 4,819,834 A | 4/1989 | Thiel | |
| 5,290,539 A | 3/1994 | Marecki | |
| 5,400,920 A | 3/1995 | Barnhart | |
| 5,474,758 A | 12/1995 | Kwon | |
| 5,697,532 A | 12/1997 | Wilde et al. | |

FOREIGN PATENT DOCUMENTS

| | | | |
|---|---|---|---|
| AT | 333 646 | | 12/1976 |
| GB | 1146709 | | 3/1969 |
| WO | WO 99/55600 | * | 4/1999 |

* cited by examiner

Primary Examiner—Kenneth Bomberg
(74) Attorney, Agent, or Firm—Christopher D. Gram; Ted K. Ringered; Robert W. Sprague

(57) ABSTRACT

A valve stem for use in an aerosol valve such as a metered dose medicinal aerosol valve is described. The valve stem includes a flattened area around the side hole. The flattened area helps reduce damage to the diaphragm aperture upon repeated actuation of the metered dose inhaler. Also described is a metered dose valve and a metered dose inhaler, each including the flattened valve stem of the present invention.

16 Claims, 4 Drawing Sheets

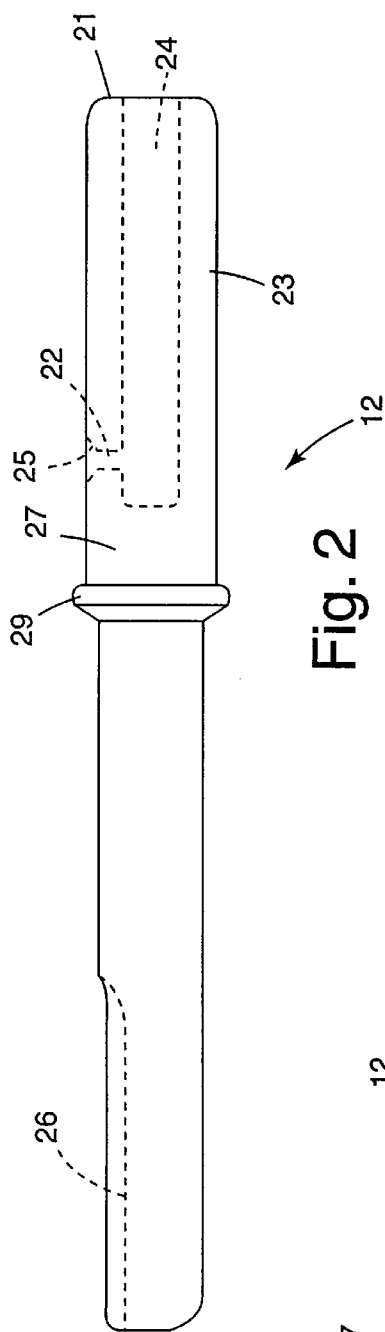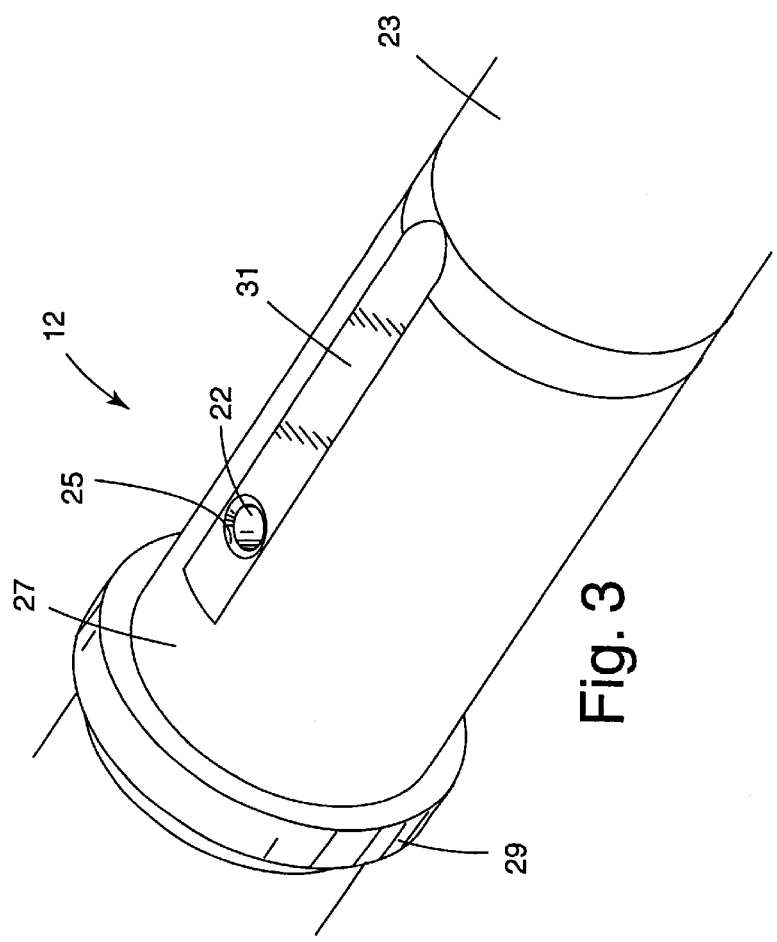

STEM CONFIGURATION TO REDUCE SEAL ABRASION IN METERED DOSE AEROSOL VALVES

This application claims priority from U.S. Provisional Application Ser. No. 60/240,737, filed Oct. 16, 2000.

TECHNICAL FIELD

This invention relates to valve stems for medicinal aerosol products and the manufacture of such devices.

BACKGROUND OF THE INVENTION

Pressurized metered dose aerosol delivery devices, such as metered dose inhalers (MDIs), allow a patient to self-administer individual metered doses of aerosolized medicine. A typical metered dose aerosol valve includes a metering chamber and a valve stem that slides through a diaphragm, also known as an outer stem gasket or seal, into the metering chamber. When not in use, the diaphragm maintains a closed seal around the valve stem. The valve stem includes a side hole in communication with a passageway inside the valve stem. When actuated, the side hole slides past the diaphragm and into the metering chamber. The side hole and passageway thus provide an outlet through which the metered dose of aerosol escapes the metering chamber. In the case of an MDI, the aerosolized medicine escapes the metering chamber and becomes accessible for oral or nasal inhalation by the patient.

The seal formed between the valve stem and the diaphragm gasket is critical. The diaphragm, typically made from an elastomeric material, must a) maintain the seal with the valve stem in order to prevent leakage of the aerosol formulation, and b) permit smooth, reliable valve operation. Leakage alters the relative concentration of the drug in the formulation being delivered to the patient. At the same time, the seal must permit smooth operation as the valve stem slides into and out of the metering chamber during actuation of the aerosol delivery device.

One problem observed in MDIs is that sharp edges of the side hole can damage the diaphragm upon repeated actuation of the MDI. Damage to the diaphragm is observed regardless of whether the valve stem is made of metal or plastic. Such damage to the diaphragm can degrade the seal between the diaphragm and the valve stem, thereby corrupting dose metering and contaminating the aerosol with particles of diaphragm material. Damage to the diaphragm may also block or partially block delivery of the aerosol. This may occur directly, such as by accumulation of diaphragm fragments. Alternatively, the effect may be indirect; the abraded particles may act as "seeding" for crystallization of the aerosol. Delivery of the aerosol may be completely or partially blocked by accumulated diaphragm particles, crystallized aerosol, or both.

One approach to solve the problem of damage to the diaphragm by the edges of the side hole is to provide a side hole with rounded or beveled edges. This is done deliberately during the manufacture of metal valve stems. When the side hole is punched into the valve stem, the surrounding metal is bent inward, resulting in rounded edges. International Publication No. WO 99/55600 describes side hole edges that are drilled, then countersunk in order to obtain rounded edges. No equivalent shaping of the side hole edges has been applied to plastic valve stems.

Damage to the diaphragm still has been observed in aerosol delivery devices, even those having a side hole with rounded or beveled edges. Therefore, a continuing need exists for an aerosol valve stem that reduces damage to the diaphragm upon repeated actuation.

SUMMARY OF THE INVENTION

It has now been found that the geometry of a round hole on a cylindrical surface is an important contributor to the damage done to the diaphragm upon actuation of a metered dose aerosol delivery device, even when the side hole has rounded or beveled edges. The aerosol valve stem configuration of the present invention significantly reduces diaphragm seal abrasion.

The valve stem of a metered dose aerosol delivery device is generally cylindrical and the side hole is positioned perpendicular the valve stem axis. Because the side hole is located on a cylindrical surface, the edges of the side hole define a shape similar to that of a saddle, presenting sharp edges at the top and the bottom of the side hole. These sharp edges have a tendency to damage the surface of the diaphragm each time the side hole passes through the diaphragm aperture. After repeated actuation of the device, the damage can be sufficient to cause particles to be abraded from the diaphragm, thereby reducing sealing performance. Such damage to the diaphragm also results in particles contaminating the aerosolized medicine being delivered to the patient.

Rounded or beveled edges of the side hole do not eliminate degradation of the diaphragm by the edges of the side hole; the side hole edges still possess the raised profile of the saddle shape inherent in a round hole on a cylindrical surface.

The present invention provides an aerosol valve stem in which the area around the side hole is flattened. The invention is particularly well suited for use in a metered dose aerosol delivery device such as an MDI, because the edges of the side hole define a planar circle or, at least, a very shallow saddle. The geometry of the side hole minimizes abrasion of the diaphragm as the side hole passes through the diaphragm aperture.

One embodiment of the invention provides a generally cylindrical aerosol valve stem having a tip at one end and a body wall defining a hollow core extending axially from the tip into the body. A side hole pierces the body wall of the valve stem and is in communication with the hollow core. Finally, there is a flattened area around the side hole so that abrasion of the diaphragm gasket by the edges of the side hole is reduced.

The edges of the side hole may be rounded or beveled in order to further decrease the abrasive effects of the side hole passing through the diaphragm aperture. The flattened area may be so flattened so as to provide a planar surface surrounding the side hole. In one configuration, the flattened area may be limited to the area adjacent to the side hole. Alternatively, the flattened area may extend to the tip of the valve stem, into the sealing area of the valve stem, or both. In each configuration, the aerosol valve stem of the invention significantly reduces diaphragm seal abrasion.

Another embodiment of the invention provides a metered dose valve including an aerosol valve stem as described above.

Another embodiment of the invention provides for a metered dose inhaler including an aerosol valve stem as described above.

Accordingly, the present invention provides an aerosol valve stem including: a generally cylindrical body having a tip at one end and a body wall defining a hollow core extending axially from the tip into the body, a side hole through the body wall in fluid communication with the hollow core, and a flattened area around the hole.

In another aspect the invention provides a device for delivering an aerosol including: a generally cylindrical body having a tip at one end and a body wall defining a hollow core extending axially from the tip into the body, a side hole through the body wall in fluid communication with the hollow core, and a flattened area around the hole; a diaphragm having walls defining a diaphragm aperture; a casing member having walls defining a formulation chamber and a casing aperture; wherein the valve stem passes through the diaphragm aperture and the casing aperture and is in slidable sealing engagement with the diaphragm aperture, and wherein the diaphragm is in sealing engagement with the casing member; and a metering chamber of a predetermined volume and having an inlet end, an inlet aperture and an outlet end, wherein the outlet end is in sealing engagement with the diaphragm, and wherein the valve stem passes through the inlet aperture and is in slidable engagement with the inlet end of the metering chamber, and wherein the valve stem is movable between an extended, closed position, in which the inlet end of the metering chamber is open and the outlet end is closed, and a compressed, actuated position in which the inlet end of the metering chamber is closed and the outlet end is open.

In yet another aspect, the invention provides a method of delivering an aerosolized dose of medicine including the steps of: providing an inhaler including an aerosol valve stem including a generally cylindrical body having a tip at one end and a body wall defining a hollow core extending axially from the tip into the body, a side hole through the body wall in fluid communication with the hollow core, and a flattened area around the hole; providing a formulation of aerosolized medicine contained within the inhaler; and actuating the inhaler.

BRIEF DESCRIPTION OF THE DRAWINGS

FIG. 2 is a side view of an aerosol valve stem according to the present invention.

FIG. 3 is a close-up view of the side hole of an aerosol valve stem according to the present invention.

DETAILED DESCRIPTION OF THE INVENTION

The present invention provides an aerosol valve stem that is particularly desirable for use in metered dose medicinal aerosol products, such as MDIs. The valve stem is designed to reduce the damage caused to the diaphragm aperture of the metered dose aerosol valve by repeated actuation of the valve.

Figure 1:
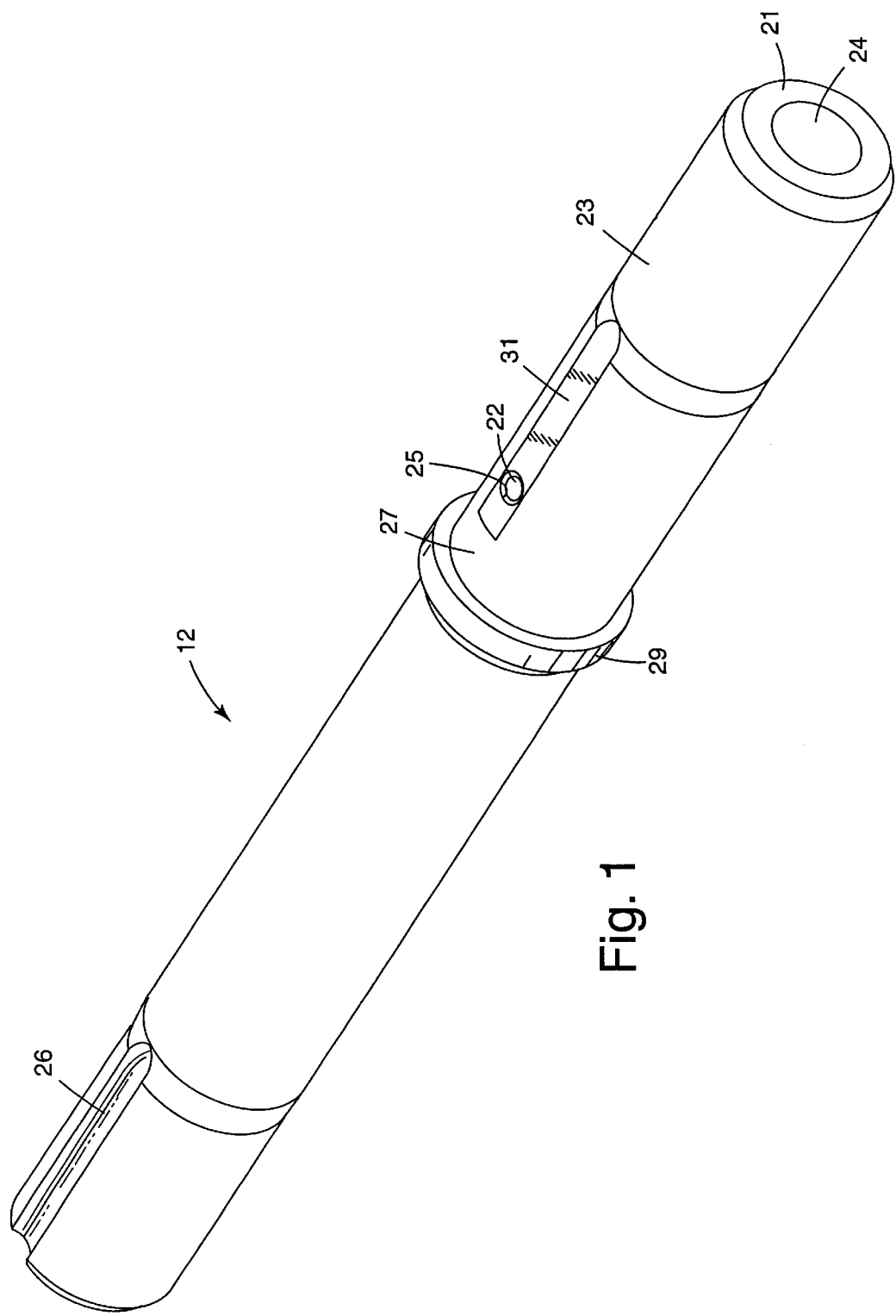
FIG. 1 is a front perspective view of an aerosol valve stem according to the present invention.

FIG. 1 illustrates the aerosol valve stem 12 according to the present invention. The valve stem includes a tip 21 at one end and a channel 26 at the other end. A hollow core 24 extends into the valve stem from the tip 21. A body wall 23 surrounds the hollow core 24. The hollow core connects to a side hole 22, as shown in FIG. 2. The side hole has an edge 25 that may be rounded, beveled or a right angle. FIG. 3 illustrates a side hole edge 25 as a beveled edge. A sealing area 27 lies between the side hole 22 and the flange 29.

Figure 4:
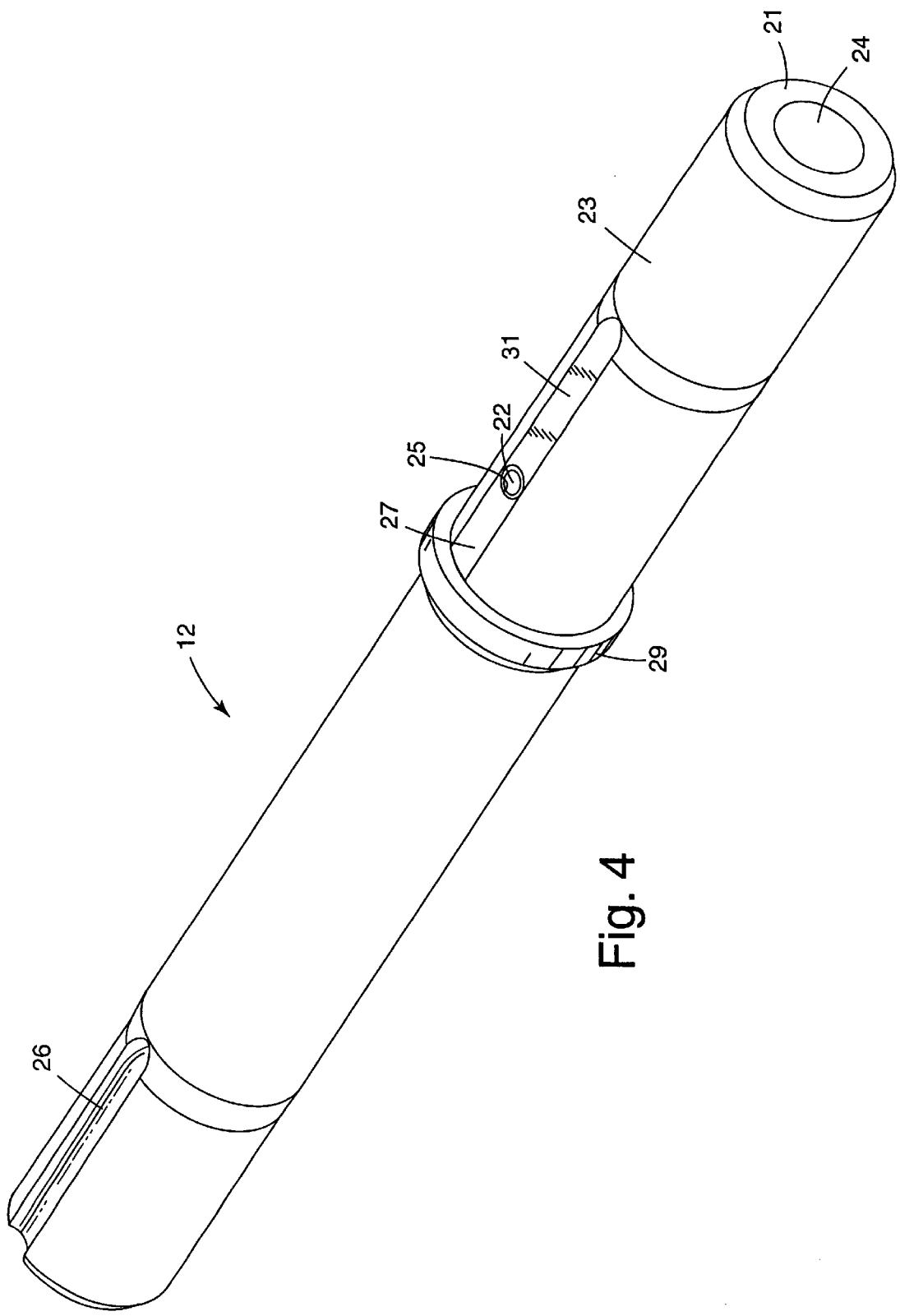
FIG. 4 is a front perspective view of an alternate embodiment of the aerosol valve stem according to the present invention.

According to the invention, the valve stem 12 includes a flattened area 31 around the side hole 22. The flattened area may be on one or more sides of the side hole. Alternatively, the flattened area may encircle the side hole completely. The sealing area 27 may or may not be included in the flattened area 31. FIG. 2 shows the valve stem configured so that the sealing area is outside the flattened area. In another embodiment, the flattened area includes the sealing area, as shown in FIG. 4. When the flattened area provides a planar surface, the edge of the side hole 25 defines a planar circle. Regardless of the particular embodiment, the aerosol valve stem of the invention significantly reduces abrasion of the diaphragm seal by the edges of the side hole.

Figures 5, 6:
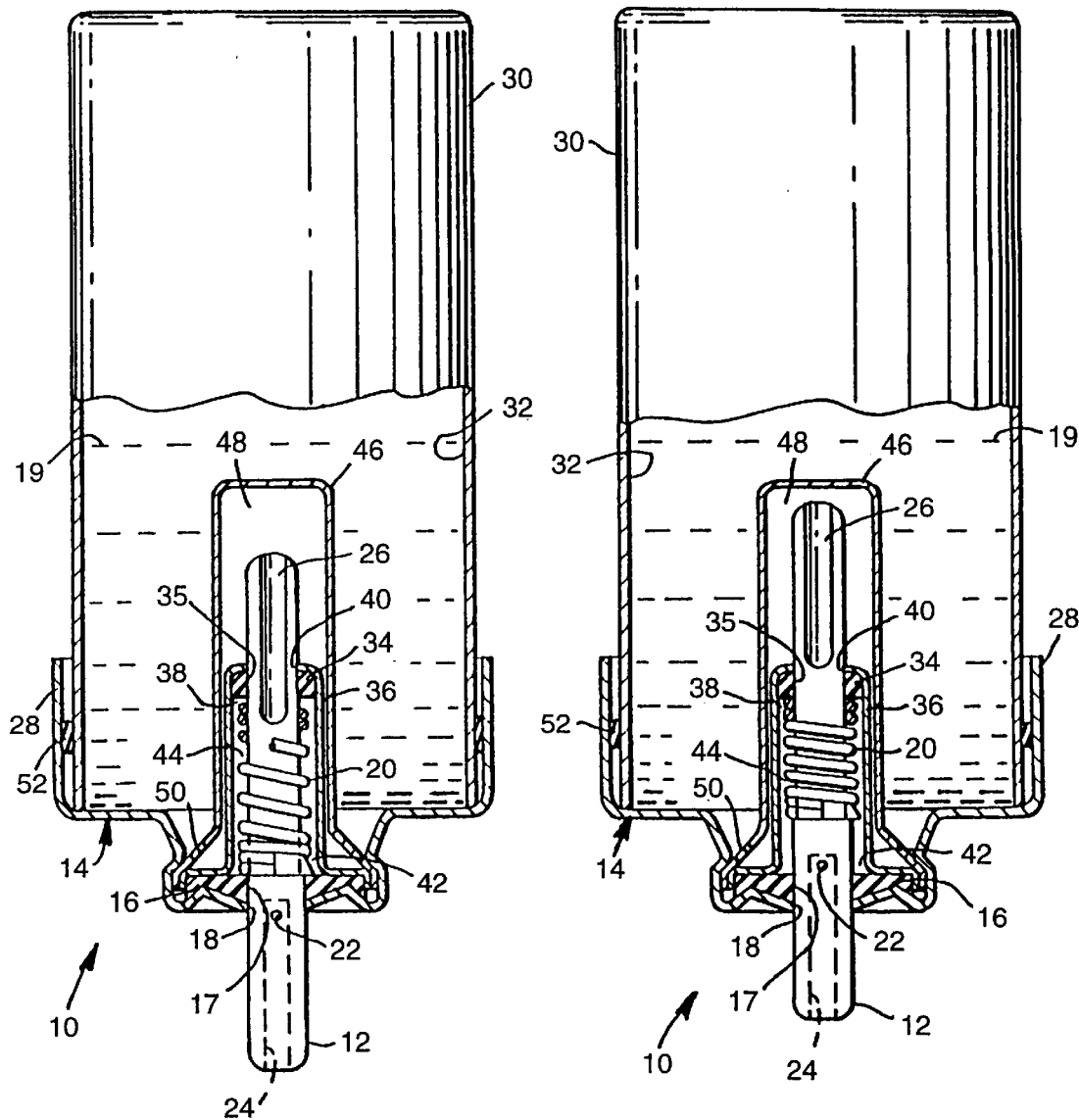
FIG. 5 illustrates the metered dose valve of the present invention in an extended, closed position.
FIG. 6 illustrates the metered dose valve of the present invention in a compressed, actuated position.

FIGS. 5 and 6 illustrate a metered dose inhaler 10 including the valve stem 12 of the present invention. The inhaler 10 includes the valve stem 12, a casing member 14 and a diaphragm 16. The casing member has walls defining a casing aperture 18 and the diaphragm has walls defining diaphragm aperture 17. The valve stem 12 passes through and is in slidable sealing engagement with the diaphragm aperture 17 at the sealing area 27. The diaphragm is also in sealing engagement with the casing member 14. The casing member 14 includes a mounting cup 28 and a canister body 30 and defines a formulation chamber 32. A sealing member 52 substantially seals the canister body 30 and the mounting cup 28. The sealing member 52 is preferably an O-ring including an elastomeric material.

The inhaler 10 further includes a chamber seal 34 having walls defining a chamber seal aperture 35, and metering chamber 36 having an inlet end 38, inlet aperture 40 and outlet end 42. The metering chamber 36 is in sealing engagement with the diaphragm 16, and the valve stem 12 passes through the inlet aperture 40 and is in slidable sealing engagement with the chamber seal 34.

When the inhaler 10 is intended for use with a suspension aerosol formulation, it may include a retaining cup 46 fixed to a mounting cup 28 and having walls defining a retention chamber 48 and aperture 50. When intended for use with a solution aerosol formulation, the retaining cup 46 is optional.

Operation of the metered dose inhaler 10 is illustrated in FIGS. 5 and 6. In FIG. 5, the inhaler is in the extended, closed position. Aperture 50 allows open communication between the retention chamber 48 and the formulation chamber 32, thus allowing the aerosol formulation to enter the retention chamber. The channel 26 allows open communication between the retention chamber 48 and the metering chamber 36, thus allowing a predetermined amount of aerosol formulation to enter the metering chamber through the inlet aperture 40. The diaphragm 16 seals the outlet end 42 of the metering chamber.

FIG. 6 illustrates the metered dose inhaler 10 in the compressed, actuated position. As the valve stem 12 is depressed, the channel 26 is moved relative to the chamber seal 34 such that inlet aperture 40 and chamber seal aperture 35 are substantially sealed, thus isolating a metered dose of formulation inside the metering chamber 36. Further actuation of the valve stem causes the side hole 22 to pass through aperture 18 and into the metering chamber, whereupon the metered dose of aerosolized medicine is exposed to ambient pressure. Rapid vaporization of the propellant causes the aerosolized medicine to be forced through the side hole 22, through the hollow core 24, out the tip 21 of the valve stem, and into a patient port such as a mouthpiece. The patient receives the aerosolized medicine by inhaling the metered dose from the mouthpiece.

The aerosol valve stem of the invention may be made of any suitable material, such as metal or plastic. Aerosol valve stems made from drawn metal may have the side hole introduced by piercing with a suitably shaped tool according to standard metalworking practices. The flattened area may then be ground and buffed on the drawn metal valve stem, thus producing a smooth flattened surface that will minimize abrasion of the diaphragm seal.

A plastic aerosol valve stem may be molded either as a single piece or as two parts that are subsequently assembled to form the valve stem. The side hole and the flattened area are preferably molded into the valve stem. This can be achieved either by shaping the mold with the flattened region or by providing a larger than usual side hole. The latter approach allows valve stems to be molded so that parting lines a) do not interfere with the sealing, and b) do not present their own sharp surfaces to the seal.

Alternatively, the aerosol valve stem may be molded without the side hole, flattened area, or both. In that case, these feature(s) can be introduced to the valve stem after molding. The flattened area may be introduced to the valve stem by grinding the area around the hole flat, then finishing the area to present a smooth, flattened surface that will minimize abrasion of the diaphragm seal.

The side hole may be introduced by piercing the valve stem with a suitably shaped tool. The piercing may be done while the aerosol valve stem is still in the molding press. If the piercing occurs while the aerosol valve stem is still hot enough, it may be achieved with less surface damage or elastic "spring back." This may be achieved by designing the tool with increased thermal capacity in the area around the hole, thereby creating a valve stem that is still hot in that area. Alternatively, the area around the side hole may be precooled to cause deliberate underfilling the area, thereby resulting in rounded edges.

OTHER EMBODIMENTS

The foregoing description is intended to illustrate and not limit the scope of the invention, which is defined by the scope of the appended claims. Other aspects, advantages and modifications are within the scope of the following claims.

What is claimed is:

1. An aerosol valve stem comprising:
   a generally cylindrical body having a tip at one end and a body wall defining a hollow core extending axially from the tip into the body;
   a side hole through the body wall in fluid communication with the hollow core; and
   a flattened area around the hole comprising a sealing section adjacent to the side hole.

2. The aerosol valve stem of claim 1 in which the side hole has an edge that is a planar circle.

3. The aerosol valve stem of claim 1 in which the flattened area entirely surrounds the hole.

4. The aerosol valve stem of claim 1 in which the edge of the side hole is beveled.

5. The aerosol valve stem of claim 1 in which the edge of the side hole is rounded.

6. The aerosol valve stem of claim 1 in which the flattened area around the side hole extends from the sealing section to the tip of the valve stem.

7. A metered dose valve comprising the aerosol valve stem of claim 1.

8. A metered dose inhaler comprising the aerosol valve stem of claim 1.

9. A device for delivering an aerosol comprising the valve stem of claim 1.

10. A method of delivering an aerosolized dose of medicine comprising:
    providing an inhaler comprising the valve stem of claim 1;
    providing a formulation of aerosolized medicine contained within the inhaler; and
    actuating the inhaler.

11. An aerosol valve stem comprising;
    a generally cylindrical body having a tip at one end and a body wall defining a hollow core extending axially from the tip into the body;
    a side hole through the body wall in fluid communication with the hollow core, and comprising a beveled edge; and
    a flattened area around the hole.

12. The aerosol valve stem of claim 11 further comprising a sealing section adjacent to the side hole.

13. The aerosol valve stem of claim 12 wherein the sealing section is substantially cylindrical.

14. An aerosol valve stem comprising:
    a generally cylindrical body having a tip at one end and a body wall defining a hollow core extending axially from the tip into the body;
    a side hole through the body wall in fluid communication with the hollow core, and comprising a rounded edge; and
    a flattened area around the hole.

15. The aerosol valve of claim 14 further comprising a sealing section adjacent to the side hole.

16. The aerosol valve stem of claim 15 wherein the sealing section is substantially cylindrical.

* * * * *